United States Patent [19]

Patent Number: 5,977,106

Patoiseau et al.

Date of Patent: Nov. 2, 1999

[54] 3,5-DIOXO-(2H,4H)-1,2,4-TRIAZINE DERIVATIVES

[75] Inventors: Jean-François Patoiseau, Castres; Christian Faure, Toulouse; Elisabeth Dupont-Passelaigue, Castres; Françoise Couret, Corransac; Wouter Koek, Viviers-les-Montagnes, all of France

[73] Assignee: Pierre Fabre Medicament, Boulogne, France

[21] Appl. No.: 08/849,655

[22] PCT Filed: Dec. 1, 1995

[86] PCT No.: PCT/FR95/01589

§ 371 Date: May 30, 1997

§ 102(e) Date: May 30, 1997

[87] PCT Pub. No.: WO96/16949

PCT Pub. Date: Jun. 6, 1996

[30] Foreign Application Priority Data

Dec. 2, 1994 [FR] France ................................ 94 14544

[51] Int. Cl.⁶ ...................... C07D 253/075; A61K 31/53
[52] U.S. Cl. ............................................. 514/242; 544/182
[58] Field of Search ............................... 544/182; 514/242

Primary Examiner—John M. Ford
Attorney, Agent, or Firm—Rockey, Milnamow & Katz, Ltd.

[57] ABSTRACT

Novel 3,5-dioxo-(2H,4H-triazine derivatives of general formula (I): wherein $R_1$ is hydrogen, a $C_1$–$C_4$ alkyl radical, phenyl $C_1$–$C_4$ alkyl or phenyl, the phenyl ring being optionally substituted by one or more groupings such as ($C_1$–$C_3$) alkyl, hydroxyl, trifluoromethyl or halogen: $R_2$ is hydrogen or a ($C_1$–$C_4$) alkyl radical, n can be an integer from 2 to 6; A is a grouping of the aryl piperazino or benzodioxanyl-methylamino or pyridodioxanyl-methylamino type. The invention also concerns a method of preparing said derivatives and pharmaceutical compositions comprising at least one of the compounds of general formula (I) as the active ingredient:

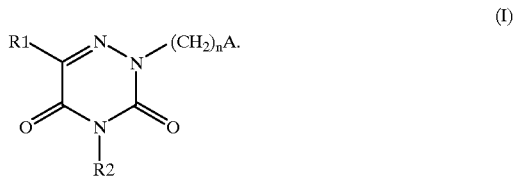

5 Claims, No Drawings

3,5-DIOXO-(2H,4H)-1,2,4-TRIAZINE DERIVATIVES

This is a 371 of PCT/FR45/01589, filed Dec. 1, 1995.

The subject of the present invention is novel 3,5-dioxo-(2H,4H)-1,2,4-triazine derivatives functionalized at the 2-position, their preparation and their therapeutic use.

Within the framework of the search for new anxiolytic medicaments with a non-benzodiazepine profile, the discovery and the development of buspirone have triggered a large number of studies. Numerous observations make it possible to associate a dysfunction of the serotoninergic system with certain psychiatric pathologies such as anxiety or depression (M. Hamon, H. Gozlan, Medecine/Sciences 1993, 9, 21–30). Thus, during the past few years, numerous compounds with affinity towards the $5HT_{1A}$ receptors have been claimed for their benefit in human therapy and more particularly for their anxiolytic activity (J. Peergaard et al., current opinion in therapeutic patents, January 1993, 101–128).

3,5-dioxo-6-amino-(2H,4H)-1,2,4-triazine derivatives have been claimed by the applicant for their application in human therapy (FR filing No. 93,08259/06.07.93).

The compounds of the present invention are characterized by their novel structure, their potent affinity towards the $5HT_{1A}$ receptor and their pharmacological profile.

The compounds of the invention correspond to the formula I,

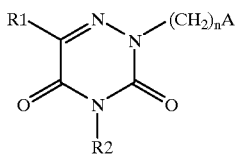

in which
$R_1$ represents hydrogen, a $(C_1-C_4)$ alkyl, phenyl $(C_1-C_4$ alkyl) or phenyl radical, the phenyl ring being optionally substituted by one or more groups such as $(C_1-C_3)$ alkyl, hydroxyl, trifluoromethyl or halogen,
$R_2$ represents hydrogen or a $(C_1-C_4)$ alkyl radical,
n can be an integer from 2 to 6,
A represents a group of the type
arylpiperazino II

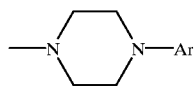

the Ar group itself representing an aromatic structure such as phenyl, naphthyl, pyrimidyl, pyridyl, optionally substituted by one or more groups such as $(C_1-C_3)$ alkyl, $(C_1-C_3)$ alkoxy, hydroxyl, trifluoromethyl or halogen, benzodioxanylmethylamino or pyridodioxanylmethylamino III

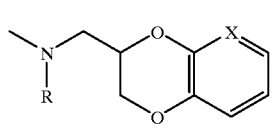

in which R represents hydrogen or a $(C_1-C_3)$ alkyl group and X represents a nitrogen or carbon atom.

In addition, the invention covers the salts of compounds of general formula I with pharmaceutically acceptable acids, as well as the various enantiomers in the case of compounds having an asymmetric carbon.

In particular, n can take the values 2, 3 or 4.

The compounds of the invention may be obtained according to two different synthesis routes.

Method A

It is characterized in that:

1—a compound of general formula IV

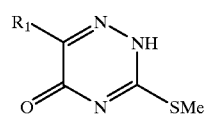

in which $R_1$ is as defined in the formula I, is treated with a dihalogenated derivative of formula V

in which n is as defined in the formula I, and Hal and Hal' represent a halogen, preferably respectively chlorine for Hal and bromine for Hal'. The reaction is carried out in dimethylformamide in the presence of sodium hydride.

2—After acid hydrolysis, treatment is performed with a derivative of formula VI or VII

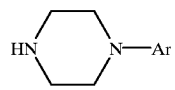

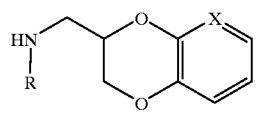

in which Ar, R and X are as defined in the formulae I, II and III.

The reaction is performed by heating in toluene or xylene or in butanol in the presence of triethylamine.

3—Treatment is optionally performed with a derivative $R_2Y$ in which $R_2$ is as defined in the formula I and Y representing chlorine, bromine or iodine, in dimethyl formamide in the presence of sodium hydride.

Method B

It is characterized in that:

1—A compound of formula VIII:

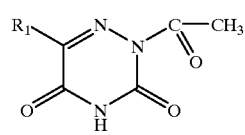

in which $R_1$ is as defined in the formula I, is treated with an alkyl halide $R_2Y$, in dimethylformamide in the presence of sodium hydride.

2—Deacetylation is performed in acid medium such as paratoluenesulfonic acid in ethanol.

3—Treatment is performed with a dihalogenated compound V as defined above, in dimethylformamide in the presence of sodium hydride, then with a derivative VI or VII, as defined above.

The intermediate and final compounds may be, if desired, purified according to one or more purification methods chosen from extraction, filtration, silica gel chromatography and crystallization.

The raw materials used in the processes described above are commercially or easily accessible to persons skilled in the art according to processes described in the literature.

The following examples illustrate the invention without limiting its scope.

The elemental analyses and the IR and NMR spectra confirm the structures of the compounds obtained according to the invention.

EXAMPLE 1

2-[4-(4-(3-trifluoromethylphenyl)piperazino)butyl]-3,5-dioxo-(2H,4H)-1,2,4-triazine hydrochloride 1 (method A)

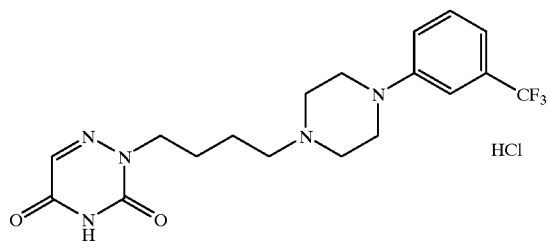

a) 2-(4-chlorobutyl)-3-methylthio-5-oxo-(2H)-1,2,4-triazine 1a

A solution of 3-methylthio-5-oxo-(2H)-1,2,4-triazine (11.45 g; 0.08 mol) in DMF (100 ml) is added dropwise to a 60% suspension of sodium hydride in paraffin oil (3.52 g; 0.088 mol) in DMF (40 ml). After stirring for one hour at room temperature, 1-bromo-4-methylthio-5-oxo-(2H)-1,2,4-triazine (11.45 g; 0.08 mol) in DMF (100 ml) is added.

After stirring for one hour at room temperature, 1-bromo-4-chlorobutane (15 g; 0.088 mol) is added and kept stirring overnight. After concentrating to dryness under vacuum, the residue is taken up in water (20 ml) and extracted with methylene chloride (2×50 ml). The organic phases are dried (Na$_2$SO$_4$) and concentrated to dryness under vacuum to give the compound 1a in the form of a brown oil (12.4 g).

TLC: Merck 60F254 silica gel
Toluene-dioxane-triethylamine 80-15-5
Rf=0.33.

b) 2-(4-chlorobutyl)-3,5-dioxo-(2H,4H)-1,2,4-triazine 1b

The compound 1a (16 g) is heated in 2 N hydrochloric acid (80 ml) at 100° C. for 30 minutes. After cooling, the mixture is extracted with methylene chloride (2×50 ml). The organic phases are dried (Na$_2$SO$_4$), evaporated to dryness under vacuum and then taken up in boiling ethyl ether (100 ml). After concentrating under vacuum and impasting with toluene, the compound 1b (2.62 g) is obtained by filtration and drying at 60° C. under vacuum.

m.p.=93° C.
TLC: Merck 60F254 silica gel
CHCl$_3$-MeOH 95-5; Rf=0.35.

c) 2-(4-(4-(3-trifluoromethylphenyl)piperazino)butyl)-3,5-dioxo-(2H,4H)-1,2,4-triazine hydrochloride 1

The compound 1b (6.67 g; 0.033 mol) and 4-(3-trifluoromethylphenyl)piperazine (15.3 g; 0.066 mol) are heated to dryness for 7 hours at 120–130° C. Xylene (40 ml) is added and heated for one additional hour under reflux.

After cooling and concentrating to dryness under vacuum, the residue is taken up in water (30 ml) and in ethyl ether (2×100 ml). The organic phases are dried (Na$_2$SO$_4$) and concentrated to dryness under vacuum. The oil obtained is taken up in ethyl ether (50 ml) and then supplemented, dropwise, with hydrochloric acid in ethyl ether (20 ml). A solid is drained which is crystallized from ethanol (50 ml). After filtration, washing with ethyl ether and drying under vacuum at 80° C., the compound 1 (3.77 g) is obtained.

m.p.=200° C.
TLC: Merck 60F254 silica gel
CHCl$_3$-MeOH 95-5; Rf=0.27.

EXAMPLE 2

4-methyl-2-(4-(4-(3-trifluoromethyl-phenyl)piperazino)butyl)-3,5-dioxo-(2H,4H) -1,2,4-triazine 2

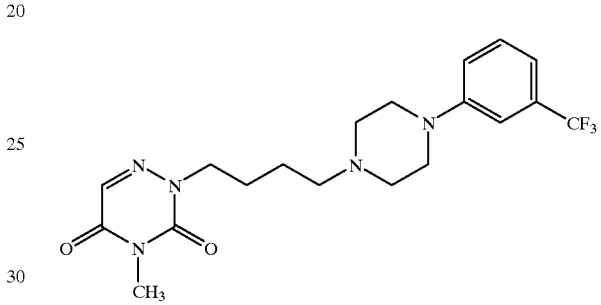

The compound 1 (3.77 g; 0.009 mol is added dropwise to a 60% suspension of sodium hydride in paraffin oil (0.77 g; 0.019 mol) in DMF (50 ml), followed, after stirring for 2 hours at room temperature, by iodomethane (1.4 g; 0.01 mol). After leaving overnight at room temperature, the mixture is concentrated to dryness under vacuum and then the residue is taken up in water (100 ml) and extracted with ethyl ether (2×50 ml). The dried organic phases (Na$_2$SO$_4$) are concentrated to dryness under vacuum to give an oil which crystallizes slowly.

After recrystallization from 2-propanol and drying under vacuum at 60° C., a compound 2 (2 g) is obtained.

m.p.=77° C.
TLC: Merck 60F254 silica gel
CHCl$_3$-MeOH 95-5; Rf=0.52.

EXAMPLE 3

4-methyl-2-(4-(4-(3-trifluoromethylphenyl)piperazino)butyl)-3,5-dioxo-(2H,4H)-1,2,4-triazine hydrochloride 3

The compound 2 (1.9 g) taken up in ethyl ether (40 ml) is supplemented with a solution of hydrochloric acid in ethyl ether. The white precipitate obtained is, after filtration, recrystallized from ethanol (60 ml) and dried under vacuum at 80° C. to give the compound 3 (1.5 g).

m.p.=225° C.
TLC: Merck 60F254 silica gel
CHCl$_3$-MeOH 95-5; Rf=0.52.

EXAMPLE 4

4-methyl-2-(4-(4-(3-chlorophenyl)piperazino)butyl)-3,5-dioxo-(2H,4H)-1,2,4-triazine 4 (method B)

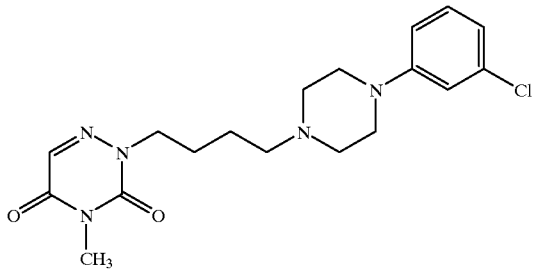

a) 2-acetyl-3,5-dioxo-(2H,4H)-1,2,4-triazine 4a

Azauracil (50 g) is treated for 80 minutes in refluxing acetic anhydride (300 ml). After cooling and concentrating to dryness under vacuum, the compound 4a (62.2 g) is obtained by impasting with toluene (300 ml).
m.p.=148° C.
TLC: 60F254 silica gel
CHCl$_3$-MeOH 90-10; Rf=0.38.

b) 4-methyl-3,5-dioxo-(2H,4H)-1,2,4-triazine 4b

The compound 4a (1.55 g; 0.01 mol) is added to a 60% suspension of sodium hydride (0.44 g; 0.011 mol) in DMF (25 ml). After stirring for 1 hour at room temperature, iodomethane (1.56 g; 0.011 mol) is added and the mixture is kept stirring overnight. After concentrating to dryness under vacuum, the residue is taken up in ethanol and p-toluenesulfonic acid (0.2 g) and then heated for 2 hours under reflux. After concentrating to dryness under vacuum and taking up in water (5 ml), the mixture is extracted with methylene chloride, the organic phases are dried (Na$_2$SO$_4$) and concentrated to dryness under vacuum. After recrystallization from toluene (7 ml) and drying at 50° C., the compound 4b (0.74 g) is obtained.
m.p.=173° C.
TLC: Merck 60F254 silica gel
CHCl$_3$-MeOH 95-5; Rf=0.49.

c) 4-methyl-2-(4-chlorobutyl)-3,5-dioxo-(2H,4H)-1,2,4-triazine 4c

The compound 4b (7.11 g; 0.056 mol) in DMF (70 ml) is added to a 60% suspension of sodium hydride (2.46 g; 0.062 mol) in DMF (25 ml). After stirring for 2 hours at room temperature, 1-bromo-4-chlorobutane (10.55 g; 0.062 mol) is added and the mixture is kept stirring overnight. After concentrating to dryness under vacuum, the residue is taken up in water (15 ml) and extracted with ethyl ether (2×50 ml). The organic phases, dried (Na$_2$SO$_4$) and concentrated to dryness under vacuum, give the oily compound 4c.
TLC: Merck 60F254 silica gel
Toluene-ethyl acetate 70-30; Rf=0.47.

d) 4-methyl-2-(4-(4-(3-chlorophenyl)piperazino)butyl)-3,5-dioxo-(2H,4H)-1,2,4-triazine 4

The compound 4c (5.5 g; 0.025 mol) and 4-(3-chlorophenyl)piperazine (9.83 g; 0.05 mol) are heated for 3 hours in refluxing butanol (150 ml) in the presence of triethylamine (10 ml). The mixture is concentrated to dryness under vacuum, taken up in water and then extracted with ethyl ether (2×50 ml). The dried organic phases (Na$_2$SO$_4$) are concentrated to dryness under vacuum to give an oil which crystallizes from isopropyl ether (70 ml). After recrystallization from 2-propanol and drying under vacuum at 40° C., the compound 4 (4.24 g) is obtained.

m.p.=60–62° C.
TLC: Merck 60F254 silica gel
CHCl$_3$-MeOH 95-5; Rf=0.41.

EXAMPLE 5

4-methyl-2-(4-(4-(3-chlorophenyl)piperazino)butyl)-3,5-dioxo-(2H,4H)-1,2,4-triazine hydrochloride 5

The compound 4 (2.5 g) is taken up in ethanol (50 ml) and supplemented with a saturated hydrochloric acid solution in ethanol. After filtration, the precipitate is impasted in boiling ethanol (50 ml), drained, washed with ethyl ether and dried under vacuum at 80° C. to give 5 (2.68 g).

m.p.=239° C.
TLC: Merck 60F254 silica gel
CHCl$_3$-MeOH 95-5; Rf=0.43.

EXAMPLE 6

6-phenyl-2-(4-(4-(3-trifluoromethylphenyl)piperazino)butyl)-3,5-dioxo-(2H,4H)-1,2,4-triazine hydrochloride 6

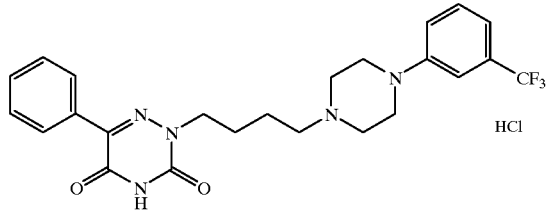

This compound is prepared according to the process described in example 1, using in stage a) 3-methylthio-5-oxo-6-phenyl-(2H)-1,2,4-triazine.

m.p.=100° C.
TLC: Merck 60F254 silica gel
CHCl$_3$-MeOH 95-5; Rf=0.42.

EXAMPLE 7

4-methyl-6-phenyl-2-(4-(4-(3-trifluoromethylphenyl)-piperazino)-butyl-3,5-dioxo-(2H,4H)-1,2,4-triazine hydrochloride 7

This compound is prepared from the compound 6 according to the processes described in examples 2 and 3.

m.p.=89° C.
TLC: Merck 60F254 silica gel
Toluene-dioxane-triethylamine 80-15-5; Rf=0.49.

EXAMPLE 8

2-[4-(4-pyrimidin-2-ylpiperazino)-butyl]-3-5-dioxo-(2H,4H)-1,2,4-triazine 8

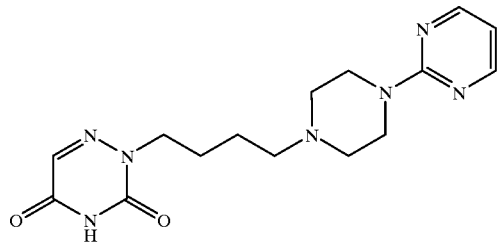

This compound is prepared according to the process described in example 1, using in stage c) 4-pyrimidin-2-ylpiperazine.

m.p.=139° C.

TLC: Merck 60F254 silica gel $CHCl_3$-MeOH 90-10; Rf=0.29.

EXAMPLE 9

4-methyl-2-(4-(4-pyrimidinyl-2)piperazino)butyl-3,5-dioxo-(2H,4H)-1,2,4-triazine 9

This compound is prepared from compound 8 according to the process described in example 2.

m.p.=93° C.

TLC: Merck 60F254 silica gel $CHCl_3$-MeOH 95-5; Rf=0.40.

EXAMPLE 10

4-methyl-2-(4-(4-(7-methoxynaphthalene-1-yl)piperazino)butyl-3,5-dioxo-(2H,4H)-1,2,4-triazine fumarate 10

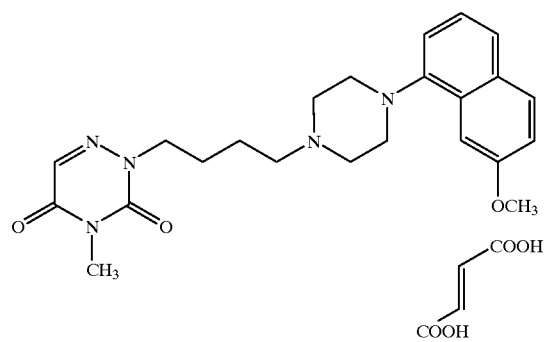

This compound is prepared according to the process described in example 4 using in stage d) 4-(7-methoxy-1-naphthyl)piperazine and by salifying with fumaric acid.

m.p.=172° C.

TLC: Merck 60F254 silica gel $CH_2Cl_2$-MeOH 90-10; Rf=0.68.

EXAMPLE 11

4-methyl-2-(4-(4-(2-methoxyphenyl)piperazino)butyl-3,5-dioxo-(2H,4H)-1,2,4-triazine 11

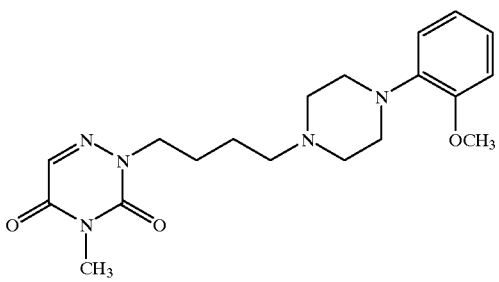

This compound is prepared according to the process described in example 4 using in stage a) 4-(2-methoxyphenyl)piperazine.

m.p.=72–74° C.

TLC: Merck 60F254 silica gel $CHCl_3$-MeOH 95-5; Rf=0.31.

EXAMPLE 12

6-methyl-2-(4-(4-(3-trifluoromethylphenyl)piperazino)butyl)-3,5-dioxo-(2H,4H)-1,2,4-triazine 12

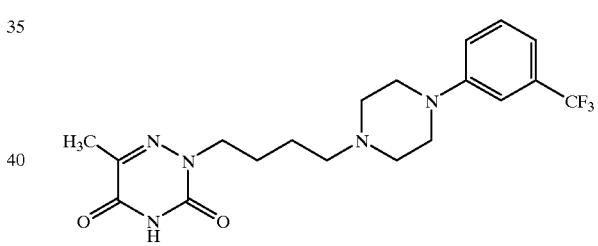

This compound is prepared according to the process described in example 1, using in stage a) 3-methylthio-6-methyl-5-oxo-(2H,4H)-1,2,4-triazine.

m.p.=123° C.

TLC: Merck 60F254 silica gel $CHCl_3$-MeOH 95-5; Rf=0.30.

EXAMPLE 13

4,6-dimethyl-2-(4-(4-(3-trifluoromethylphenyl)piperazino)butyl-3,5-dioxo-(2H,4H)-1,2,4-triazine hydrochloride 13

This compound is prepared from the derivative 12 according to the processes described in examples 2 and 3.

m.p.=208° C.

TLC: Merck 60F254 silica gel $CHCl_3$-MeOH 95-5; Rf=0.66.

EXAMPLE 14

4-methyl-2-(4-(1,4-benzodioxane-2-ylmethylamino) butyl)-3,5-dioxo-(2H,4H)-1,2,4-triazine 14

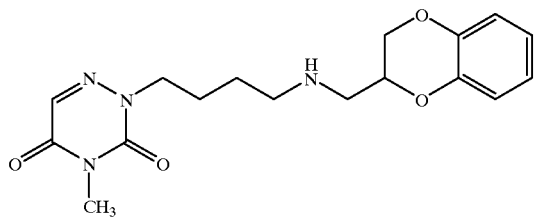

This compound is prepared according to the process described in example 4 using in stage d) 1,4-benzodioxan-2-ylmethylamine.

m.p.=70–72° C.

TLC: Merck 60F254 silica gel

CHCl$_3$-MeOH 95-5; Rf=0.31.

EXAMPLE 15

4-methyl-2-(4-(N-methyl, 1,4-benzodioxan-2-ylmethylamino)butyl)-3,5-dioxo-(2H,4H)-1,2,4-triazine fumarate 15

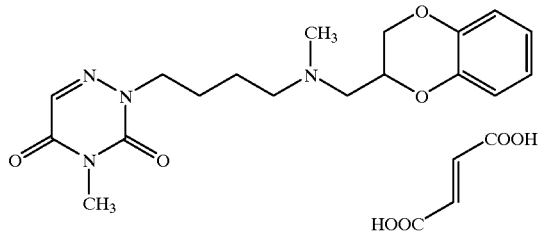

The compound 14 (1.8 g) in formic acid (48 ml) is treated with 37% formaldehyde (50 ml) at 100° C. for 10 hours. After concentrating to dryness under vacuum, the residue is taken up in water, alkalinized to pH 11 and extracted with ethyl acetate (3×200 ml). The dried organic phases (Na$_2$SO$_4$) are concentrated to dryness under vacuum and purified by flash chromatography on silica (eluant CH$_2$Cl$_2$-MeOH 95-5). The compound 15 (0.18 g) is obtained by salification with fumaric acid.

m.p.=135° C.

TLC: Merck 60F254 silica gel

CH$_2$Cl$_2$-MeOH 95-5; Rf=0.36.

EXAMPLE 16

4-methyl-2-(4-(2,3-dihydro-1,4-dioxino-[2,3-b]-pyridin-2-ylmethylamino)butyl)-3,5-dioxo-(2H,4H)-1,2,4-triazine fumarate 16

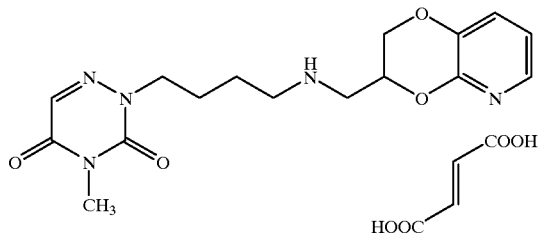

This compound is obtained according to the process described in example 4 using in stage d) 2,3-dihydro-1,4-dioxino-[2,3-b]-pyridin-2-ylmethylamine.

m.p.=147–148° C.

TLC: Merck 60F254 silica gel

CH$_2$Cl$_2$-MeOH-NH$_4$OH 90-9-1; Rf=0.40.

EXAMPLE 17

2-(3-(4-(3-trifluoromethylphenyl)piperazino)propyl)-3,5-dioxo-(2H,4H)-1,2,4-triazine 17

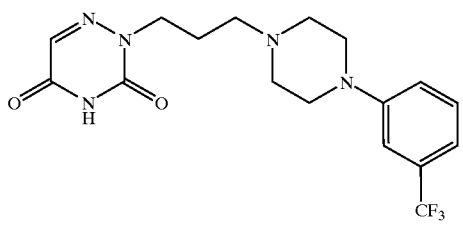

This compound is obtained according to the process described in example 1 using in stage 1a) 1-bromo-3-chloropropane.

m.p.=140° C.

TLC: Merck 60F254 silica gel

CHCl$_3$-MeOH 95-5; Rf=0.21.

EXAMPLE 18

2-(2-(4-(3-trifluoromethyl-phenyl)piperazino)ethyl)-3,5-dioxo-(2H,4H)-1,2,4-triazine hydrochloride 18

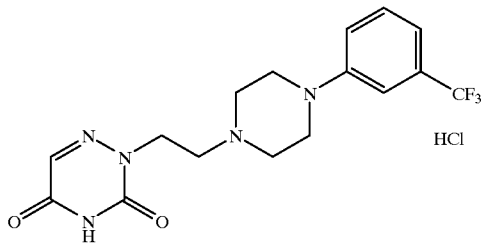

This compound is obtained according to the process described in example 1 using in stage 1a) 1-bromo-2-chloroethane.

m.p.=250° C.
TLC: Merck 60F254 silica gel
CHCl$_3$-MeOH 95-5; Rf=0.32.

EXAMPLE 19

4-methyl-2-(3-(1,4-benzodioxan-2-ylmethylamino)
propyl)-3,5-dioxo-(2H,4H)-1,2,4-triazine fumarate.

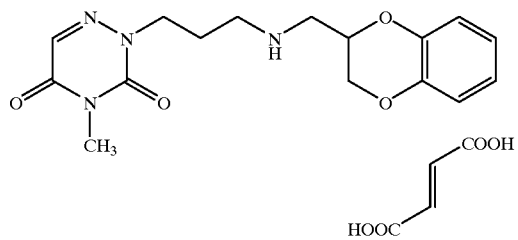

This compound is obtained according to the process described in example 4 using in stage 4c) 1-bromo-3-chloropropane and in stage 4d) 1,4-benzodioxan-2-ylmethylamine.
m.p.=161° C.
TLC: Merck 60F254 silica gel
CH$_2$Cl$_2$-MeOH 90-20; Rf=0.63.

EXAMPLE 20

4-methyl-2-(3-(2,3-dihydro-1,4-dioxino-[2,3-b]-pyridin-2-ylmethylamino)propyl)-3,5-dioxo-(2H,4H)-1,2,4-triazine fumarate 20

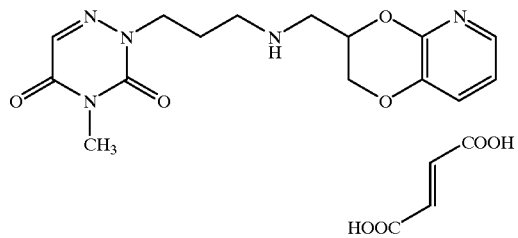

This compound is obtained according to the process described in example 4 using in stage 4c) 1-bromo-3-chloropropane and in stage 4d) 2,3-dihydro-1,4-dioxino-[2,3-b]pyridin-2-ylmethylamine.
m.p.=156° C.
TLC: Merck 60F254 silica gel
CH$_2$Cl$_2$-MeOH 90-10; Rf=0.45.

EXAMPLE 21

4-methyl-2-(4-(4-(3,4-dichloro-phenyl)piperazino)
butyl)-3,5-dioxo-(2H,4H)-1,2,4-triazine 21

This compound is prepared according to the process described in example 4 using in stage d) 4-(3,4-dichlorophenyl)piperazine.
m.p.=74° C.
TLC: Merck 60F254 silica gel
CH$_2$Cl$_2$-MeOH 95-5; Rf=0.45.

EXAMPLE 22

4-methyl-2-(4-(4-(2,3-dichloro-phenyl)piperazino)
butyl)-3,5-dioxo-(2H,4H)-1,2,4-triazine 22

This compound is prepared according to the process described in example 4 using in stage d) 4-(2,3-dichlorophenyl)piperazine.

m.p.=116° C.
TLC: Merck 60F254 silica gel
CH$_2$Cl$_2$-MeOH 95-5; Rf=0.30.

EXAMPLE 23

4-methyl-2-(4-(4-(3,5-dichloro-phenyl)piperazino)
butyl)-3,5-dioxo-(2H,4H)-1,2,4-triazine 23

This compound is prepared according to the process described in example 4 using in stage d) 4-(3,5-dichlorophenyl)piperazine.
m.p.=128° C.
TLC: Merck 60F254 silica gel
CH$_2$Cl$_2$-MeOH 95-5; Rf=0.35.

EXAMPLE 24

4-methyl-2-(4-(4-(4-chloro-2-pyrimidinyl)
piperazino)butyl-3,5-dioxo -(2H,4H) -1,2,4-triazine 24

This compound is prepared according to the process described in example 4 using in stage d) 4-(4-chloro-2-pyrimidinyl)piperazine.
m.p.=104° C.
TLC: Merck 60F254 silica gel
CH$_2$Cl$_2$-MeOH 90-10; Rf=0.55.

EXAMPLE 25

4-methyl-2-(4-(4-(4-methyl-2-pyrimidinyl)
piperazino)butyl-3,5-dioxo-(2H,4H)-1,2,4-triazine 25

This compound is prepared according to the process described in example 4 using in stage d) 4-(4-methyl-2-pyrimidinyl)piperazine.
m.p.=101° C.
TLC: Merck 60F254 silica gel
CH$_2$Cl$_2$-MeOH 90-10; Rf=0.50.

EXAMPLE 26

4-methyl-2-(4-(4-(4,6-dimethyl-2-pyrimidinyl)
piperazino)butyl)-3,5-dioxo-(2H,4H)-1,2,4-triazine 26

This compound is prepared according to the process described in example 4 using in stage d) 4-(4,6-dimethyl-2-pyrimidinyl)piperazine.
m.p.=120° C.
TLC: Merck 60F254 silica gel
CH$_2$Cl$_2$-MeOH 90-10; Rf=0.70.

EXAMPLE 27

4-methyl-2-(4-(4-(4,6-dimethyl-2-pyrimidinyl)
piperazino)butyl)-3,5-dioxo-(2H,4H)-1,2,4-triazine 27

This compound is prepared according to the process described in example 4 using in stage d) 4-(4-trifluoromethylpyrimidinyl)piperazine.
m.p.=95° C.
TLC: Merck 60F254 silica gel
CH$_2$Cl$_2$-MeOH 95-5; Rf=0.36.

EXAMPLE 28

4-methyl-2-(4-(4-(4-methoxy-2-pyrimidinyl)piperazino)butyl)-3,5-dioxo-(2H,4H)-1,2,4-triazine 28

This compound is prepared according to the process described in example 4 using in stage d) 4-(4-methoxy-2-pyrimidinyl)piperazine.

m.p.=87° C.

TLC: Merck 60F254 silica gel $CH_2Cl_2$-MeOH Rf=0.40.

EXAMPLE 29

4-methyl-2-(4-(4-(3-methoxy-2-pyridyl)piperazino)butyl)-3,5-dioxo-(2H,4H)-1,2,4-triazine fumarate 29

This compound is prepared according to the process described in example 4 using in stage d) (3-methoxy-2-pyridyl)piperazine and then by salifying with fumaric acid.

m.p.=182° C.

TLC: Merck 60F254 silica gel $CH_2Cl_2$-MeOH 90-10 Rf=0.33.

EXAMPLE 30

4-methyl-2-(4-(4-(2-pyrimidinyl)piperazino)butyl)-3,5-dioxo-(2H,4H)-1,2,4-triazine fumarate 30

This compound is obtained by salifying the compound 2 with fumaric acid.

m.p.=134° C.

TLC: Merck 60F254 silica gel $CHCl_3$-MeOH 95-5 Rf=0.40.

The compounds of the invention were subjected to pharmacological tests which demonstrated their benefit as active substances in therapy.

Thus, they were the subject of a study on their affinity for the $5\text{-HT}_{1A}$ type serotoninergic receptors.

The study of the binding to the $5\text{-HT}_{1A}$ receptor is carried out as described by Sleight and Peroutka (*Naunyn-Schmiedebergs Arch. Pharmacol.*, 343, 106–116, 1991). For these experiments, rat cerebral cortexes are used. The brain is dissected and the cortex is homogenized in 20 volumes of Tris-HCl buffer (50 mM, pH 7.4 at 25° C.) kept at 4° C. The homogenate is centrifuged at 39,000×g for 10 minutes, the centrifugation pellet is suspended in the same volume of buffer and centrifuged again. After another suspension under the same conditions, the homogenate is incubated for 10 minutes at 37° C. and then centrifuged again. The final pellet is suspended in 80 volumes of reaction buffer containing: pargyline ($10^{-5}$ M), $CaCl_2$ (4 mM) and ascorbic acid (0.1%) in Tris-HCl (50 mM, pH 7.4 at 25° C.). The final concentration of tissue in the incubation medium is 10 mg/tube.

In the saturation experiments, the reaction tubes contain 0.1 ml of various concentrations (between 0.06 and 8 nM) of [$^3$H]8-OH-DPAT, 0.1 ml of reaction buffer or 5-HT ($10^{-5}$ M, to determine the nonspecific binding) and 0.8 ml of tissue.

The displacement experiments are carried out as described by Sleight and Peroutka (*Naunyn-Schmiedebergs Arch. Pharmacol.*, 343, 106–116, 1991). All the dilutions of products to be studied are carried out in the reaction buffer. The reaction tubes contain 0.1 ml of [$^3$H]8-OH-DPAT (0.2 nM), 0.1 ml of test product 6–7 concentrations (successive 1/10 dilutions) and 0.8 ml of tissue). If the presumed affinity of the products is within the nanomolar range, the lowest concentration tested is $10^{-11}$ M, if the product has a low presumed affinity, the highest concentration tested is $10^{-4}$ M. The reaction tubes are incubated at 23° C. for 30 minutes and then rapidly filtered under vacuum on Whatman GF/B filters, the tubes are rinsed with 2×5 ml of Tris-HCl buffer (50 mM, pH 7.4 at 25° C.). The radioactivity recovered on the filter is analyzed by liquid scintillation by adding 4 ml of scintillation liquid (Emulsifer Safe, Packard). All the experiments are carried out in triplicate and repeated at least 3 times.

The dissociation constant ($K_D$) and the maximum number of binding sites (Bmax) for the radioligand are estimated from saturation experiments using the EBDA/LIGAND nonlinear regression program. This method accepts that the value of the Hill coefficient is not different from unity.

The data for the displacement experiments are analyzed respectively with the one-site and two-site models and the calculated F makes it possible to determine if the two-site model is more representative of the data obtained than the one-site model. The pKi values are given in the form of the mean SEM of 3 to 5 experiments.

Table 1 gives, by way of example, the $5\text{-HT}_{1A}$ pKi values for some derivatives of the invention, compared with Buspirone.

TABLE 1

| Affinity for the $5\text{-HT}_{1A}$ receptor | |
| --- | --- |
| Compound No. | pKi |
| 1 | 9.26 |
| 3 | 9.62 |
| 4 | 9.57 |
| 9 | 8.34 |
| 10 | 10.49 |
| 11 | 9.88 |
| 12 | 8.19 |
| 13 | 8.58 |
| 14 | 9.57 |
| 15 | 8.55 |
| 16 | 9.36 |
| 21 | 8.58 |
| 22 | 9.50 |
| 23 | 9.04 |
| 24 | 9.10 |
| 25 | 9.14 |
| 26 | 9.19 |
| 27 | 9.23 |
| 28 | 9.07 |
| 30 | 8.48 |
| Buspirone | 7.65 |

The results of the tests show that the compounds of general formula I have a high affinity for the $5\text{-HT}_{1A}$ type serotoninergic receptors.

The central activity of the compounds of the invention was evaluated for their capacity to cause the 5-HT syndrome, which is characterized by reciprocal fore-paw treading (FPT), lower-lip retraction (LLR) and flat body posture (FBP).

The experiments for the evaluation of the 5-HT syndrome are carried out in male rats (Sprague Dawley) according to the method described by F.C COLPAERT et al (*Drug Dev. Res.*, 26, 21–48; 1992).

Table 2 gives, by way of example, the active doses ($ED_{50}$) for some derivatives of the invention compared with a reference product, Buspirone.

TABLE 2

| | 5-HT syndrome | | |
| --- | --- | --- | --- |
| | $ED_{50}$:mg/kg ip | | |
| Compound No. | FBP | LLR | FPT |
| 3 | 0.31 | 0.08 | 0.31 |
| 9 | 0.08 | 0.08 | 0.31 |
| 10 | 0.02 | 0.005 | 0.02 |
| Buspirone | 5.0 | 1.25 | >40 |

The results of the tests show that the compounds of general formula I have, in vitro, a high affinity for the 5-HT$_{1A}$ type serotoninergic receptors. In vivo, they show an agonist activity at the level of these receptors.

The compounds of the invention may therefore be useful for the treatment of anxiety, depression, pain, schizophrenia, Alzheimer's disease, sleep disorders, for regulating food intake, for regulating gastric secretion, nd for treating vascular, cardiovascular and cerebro-vascular disorders, such as hypertension or migraine.

The compounds of the present invention are active on the proliferation of the T lymphocytes and may therefore be useful for the treatment of the HIV virus.

The pharmaceutical preparations containing these active ingredients may be formulated for oral, rectal or parenteral administration, for example in the form of capsules, tablets, granules, gelatin capsules, liquid solutions, syrups or oral suspensions, and contain the appropriate excipients.

It is also possible to combine therewith other pharmaceutically and therapeutically acceptable active ingredients.

We claim:

1. A compound selected from the group consisting of the 3,5-dioxo-(2H-4H)-1,2,4-triazines of the formula:

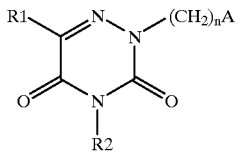

in which
R$_1$ represents hydrogen, a (C$_1$–C$_4$) alkyl, phenyl (C$_1$–C$_4$) alkyl) or phenyl radical, the phenyl ring being optionally substituted by one or more groups selected from the group consisting of (C$_1$–C$_3$) alkyl, hydroxyl, trifluoromethyl and halogen,
R$_2$ represents hydrogen or a (C$_1$–C$_4$) alkyl radical,
n is an integer from 2 to 6,
A represents an arylpiperazino group of the formula

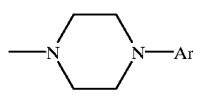

II where Ar is an aromatic structure selected from the group consisting of phenyl, naphthyl, pyrimidyl, and pyridyl, optionally substituted by one or more groups selected from the group consisting of (C$_1$–C$_3$)alkyl, (C$_1$–C$_3$) alkoxy, hydroxyl, trifluoromethyl and halogen, or a benzodioxanylmethylamino or pyridodioxanylmethylamino group of the formula

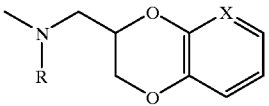

III in which R represents hydrogen or a (C$_1$–C$_3$) alkyl group and X represents a nitrogen or carbon atom as well as the addition salts with pharmaceutically acceptable acids, and the various eneatiomers in the case of compounds having an asymmetric carbon.

2. A compound according to claim 1 selected from the group consisting of:
2-(4-(4-(3-trifluoromethylphenyl)piperazino)butyl)-3,5-dioxo-(2H,4H)-1,2,4-triazine, hydrochloride,
4-methyl-2-(4-(4-(3-trifluoromethylphenyl)piperazino) butyl)-3,5-dioxo-(2H,4H)-1,2,4-triazine,
4-methyl-2-(4-(4-(3-trifluoromethylphenyl)piperazino) butyl)-3,5-dioxo-(2H,4H)-1,2,4-triazine hydrochloride,
4-methyl-2-(4-(4-(3-chlorophenyl)piperazino)butyl)-3,5-dioxo-(2H,4H)-1,2,4-triazine,
6-phenyl-2-(4-(4-(3-trifluoromethylphenyl)piperazino) butyl)-3,5-dioxo-(2H,4H)-1,2,4-triazine hydrochloride,
4-methyl-6-phenyl-2-(4-(4-(3-trifluoromethylphenyl) piperazino)butyl)-3,5-dioxo-(2H,4H)-1,2,4-triazine hydrochloride,
2-(4-(4-(2-pyrimidinyl)piperazino)butyl)-3,5-dioxo-(2H, 4H)-1,2,4-triazine,
4-methyl-2-(4-(4-(2-pyrimidinyl)piperazino)butyl)-3,5-dioxo-(2H,4H)-1,2,4-triazine,
4-methyl-2-(4-(4-(7-methoxy-1-naphthyl)piperazino) butyl)-3,5-dioxo-(2H,4H)-1,2,4-triazine fumarate,
4-methyl-2-(4-(4-(2-methoxyphenyl)piperazino)butyl)-3,5-dioxo-(2H,4H)-1,2,4-triazine,
6-methyl-2-(4-(4-(3-trifluoromethylphenyl)piperazino) butyl)-3,5-dioxo-(2H,4H)-1,2,4-triazine,
4,6-dimethyl-2-(4-(4-(3-trifluoromethylphenyl)piperazino) butyl)-3,5-dioxo-(2H,4H)-1,2,4-triazine hydrochloride,
4-methyl-2-(4-(1,4-benzodioxan-2-ylmethylamino)butyl)-3,5-dioxo-(2H,4H)-1,2,4-triazine,
4-methyl-2-(4-(N-methyl-N-1,4-benzodioxan-2-ylmethylamino)butyl)-3,5-dioxo-(2H,4H)-1,2,4-triazino fumarate,
4-methyl-2-(4-(2,3-dihydro-1,4-dioxino-[2,3-b]-pyridin-2-ylmethylamino)butyl-3,5-dioxo-(2H,4H)-1,2,4-triazine fumarate,
2-(3-(4-(3-trifluoromethylphenyl)piperazino)propyl)-3,5-dioxo-(2H,4H)-1,2,4-triazine,
2-(2-(4-(3-trifluoromethylphenyl)piperazino)ethyl)-3,5-dioxo-(2H,4H)-1,2,4-triazine hydrochloride,
4-methyl-2-(3-(1,4-benzodioxan-2-ylmethylamino)propyl)-3,5-dioxo-(2H,4H)-1,2,4-triazine hydrochloride,
4-methyl-2-(3-(2,3-dihydro-1,4-dioxino-[2,3-b]-pyridin-2-ylmethylamino)propyl)-3,5-dioxo-(2H,4H)-1,2,4-triazine fumarate,
4-methyl-2-(4-(4-(3,4-dichlorophenyl)piperazino)butyl)-3,5-dioxo-(2H,4H)-1,2,4-triazine,
4-methyl-2-(4-(4-(2,3-dichlorophenyl)piperazino)butyl)-3,5-dioxo-(2H,4H)-1,2,4-triazine,
4-methyl-2-(4-(4-(3,5-dichlorophenyl)piperazino)butyl)-3,5-dioxo-(2H,4H)-1,2,4-triazine,
4-methyl-2-(4-(4-(4-chloro-2-pyrimidinyl)piperazino) butyl)-3,5-dioxo-(2H,4H)-1,2,4-triazine,
4-methyl-2-(4-(4-methyl-2-pyrimidinyl)piperazino)butyl)-3,5-dioxo-(2H,4H)-1,2,4-triazine,
4-methyl-2-(4-(4-(4,6-dimethyl-2-pyrimidinyl)piperazino) butyl)-3,5-dioxo-(2H,4H)-1,2,4-triazine, 4-methyl-2-(4-(4-(4-trifluoromethyl-2-pyrimidinyl)piperazino)butyl)-3,5-dioxo-(2H,4H)-1,2,4-triazine, 4-methyl-2-(4-(4-(4-methoxy-2-pyrimidinyl)piperazino)butyl)-3,5-dioxo-(2H,4H)-1,2,4-triazine, 4-methyl-2-(4-(4-(3-methoxy-2-pyridyl)piperazino)butyl)-3,5-dioxo-(2H,4H)-1,2,4-triazine fumarate, and 4-methyl-2-(4-(4-(2-pyrimidinyl)piperazino)butyl)-3,5-dioxo-(2H,4H)-1,2,4-triazine fumarate.

3. A pharmaceutical composition that comprises a compound defined according to claim 1 and a pharmaceutically acceptable carrier.

4. A method of treating a condition selected from the group consisting of anxiety and depression comprising administering to a host in need of such treatment an effective amount of a compound of claim 1.

5. A process for the preparation of chemical compounds according to claim 1 characterized:

a) in that a compound of formula VIII:

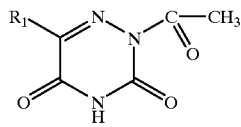

VIII in which $R_1$ is as defined in claim 1, is treated with an alkyl halide $R_2Y$ in which $R_2$ is as defined in claim 1 and Y represents chlorine, bromine or iodine; and b) the resulting compound is deacetylated in an acidic medium, then treated with a dihalogenated compound V,

V in which n is as defined in claim 1, and Hal and Hal' represent a halogen to form a derivative VI or VII

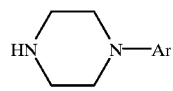

VI

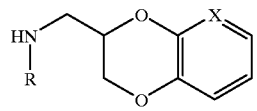

VII in which Ar, X and R are as defined in claim 1, and condensing the derivative VI or VII.

* * * * *